(12) United States Patent
Taylor, Jr.

(10) Patent No.: US 6,404,905 B1
(45) Date of Patent: Jun. 11, 2002

(54) METHOD AND APPARATUS FOR IMPRESSING A MASTER PATTERN TO A GEL IMAGE

(75) Inventor: John Taylor, Jr., Clayton, NC (US)

(73) Assignee: Large Scale Proteomics Corp., Germantown, MD (US)

( * ) Notice: Subject to any disclaimer, the term of this patent is extended or adjusted under 35 U.S.C. 154(b) by 0 days.

(21) Appl. No.: 09/653,363

(22) Filed: Aug. 31, 2000

(51) Int. Cl.[7] .................................................. G06K 9/00
(52) U.S. Cl. ....................................................... 382/128
(58) Field of Search .............................. 382/100, 128, 382/129, 133, 181, 215, 217, 218, 219, 286; 204/450, 455, 456, 471; 356/344, 391, 392, 393, 394; 430/9, 31, 32, 269

(56) References Cited

U.S. PATENT DOCUMENTS

| | | | |
|---|---|---|---|
| 4,014,000 A | 3/1977 | Uno et al. | 382/203 |
| 4,322,716 A | 3/1982 | Sternberg | 382/303 |
| 4,464,789 A | 8/1984 | Sternberg | 382/291 |
| 4,644,582 A | 2/1987 | Morishita et al. | 382/130 |
| 4,741,043 A | 4/1988 | Bacus | 382/129 |
| 4,805,123 A | 2/1989 | Specht et al. | 382/144 |
| 4,899,393 A | 2/1990 | Morishita et al. | 382/130 |
| 4,920,498 A | 4/1990 | Kaneko | 204/546 |
| 5,129,014 A | 7/1992 | Bloomberg | 382/287 |
| 5,339,176 A | 8/1994 | Smilansky et al. | 358/504 |
| 5,495,535 A | 2/1996 | Smilansky et al. | 382/145 |
| 5,581,638 A | 12/1996 | Givens et al. | 382/294 |
| 6,005,977 A | 12/1999 | Tamimizu et al. | 382/216 |
| 6,064,754 A * | 5/2000 | Parekh et al. | 382/129 |
| 6,123,821 A * | 9/2000 | Anderson et al. | 204/456 |

OTHER PUBLICATIONS

"Information Extraction from 2D Electrophoresis Images", By Thompson et al., proceeding of IEEE, 20th annual Internation conference of medicine and biology society, 1998.*
"Automatic 2–D Gel Registration Using Distance Minimization of Image Morphing", By Josso et al., IEEE, 2000.*
"Afast Structure Matching and Its Application to Pattern Analysis of 2D Electrophoresis Images", By Watanabe et al., IEEE, 1998.*

* cited by examiner

Primary Examiner—Andrew W. Johns
Assistant Examiner—Shervin Nakhjavan
(74) Attorney, Agent, or Firm—Roylance, Abrams, Berdo & Goodman, LLP

(57) ABSTRACT

A computer-implemented method analyzes a scanned image of a 2-D electrophoresis gel producing spot specific data (SSD). The computer creates an object pattern of a suitably processed scanned image and uses the spot information in the object pattern in order to warp a master pattern into alignment with the object pattern (and hence the scanned image). The object pattern is replaced with the warped master pattern, augmented by addition of well-defined spots in the object image not present in the warped master pattern, and optimized to fit a processed version of the scanned image. This new object model thus contains identifying and relative position information from the master pattern and other spot specific data (SSD) from the old object model. The new object pattern thereby forms a basis upon which to compare the scanned image with other scanned images similarly processed.

14 Claims, 6 Drawing Sheets

METHOD AND APPARATUS FOR IMPRESSING A MASTER PATTERN TO A GEL IMAGE

BACKGROUND OF THE INVENTION

A. Field of the Invention

The invention relates to a method and apparatus for computer-implemented processing and manipulation of an image in order to extract data from the image, and more specifically, the present invention relates to a method and apparatus for manipulation of a master pattern and a scanned image in order to identify information present in the scanned image by comparing the scanned image to a modified master pattern.

B. Description of Related Art

In the field of electrophoretic separations of macromolecules and two-dimensional electrophoretic separations, proteins and other biomolecular matter are separated for identification and quantitative analysis. Such two-dimensional procedures typically involve sequential separations by iso-electric focusing (IEF) and sodium dodecyl sulfate (SDS) slab gel electrophoresis using gel media for both iso-electric focusing and SDS electrophoresis.

A protein is a macromolecule composed of a chain of amino acids. Some amino acids found in proteins carry a negative charge and others carry a positive charge, in some pH range. A specific protein, defined by its specific sequence of amino acids, is thus likely to incorporate a number of charged groups along its length. The magnitude of the charge contributed by each amino acid is governed by the prevailing pH of the surrounding solution, and can vary from a minimum of 0 to a maximum of 1 charge (positive or negative depending on the amino acid), according to a titration curve relating charge and pH according to the pK of the amino acid in question. Under denaturing conditions in which all of the amino acids are exposed, the total charge of the protein molecule is given approximately by the sum of the charges of its component amino acids, all at the prevailing solution pH.

Two proteins having different ratios of charged, or titrating, amino acids can be separated by virtue of their different net charges at some pH. Under the influence of an applied electric field, a more highly charged protein will move faster than a less highly charged protein of similar size and shape. If the proteins are made to move from a sample zone through a non-convecting medium (typically a gel such as polyacrylamide), an electrophoretic separation will result.

If, in the course of migrating under an applied electric field, a protein enters a region whose pH has that value at which the protein's net charge is zero (the isoelectric pH), it will cease to migrate relative to the medium. Further, if the migration occurs through a monotonic pH gradient, the protein will "focus" at this isoelectric pH value. If it moves toward more acidic pH values, the protein will become more positively charged, and a properly-oriented electric field will propel the protein back towards the isoelectric point. Likewise, if the protein moves towards more basic pH values, it will become more negatively charged, and the same field will push it back toward the isoelectric point. This separation process, called iso-electric focusing, can resolve two proteins differing by less than a single charged amino acid among hundreds in the respective sequences.

Typically, iso-electric focusing is performed using a tube or column of medium with a prepared tissue sample deposited at the top of the tube. Current is applied between opposite ends of the tube causing the proteins in the tissue to migrate to their respective isoelectric focusing points. The medium in the tube now includes proteins that have been separated linearly along the length of the medium in the tube. The medium and proteins are next removed from the tube and loaded along one edge of an SDS slab gel for further electrophoresis. The SDS slab gel is typically a rectangular assembly that includes a separation medium retained between to glass plates. Current is applied between opposite edges of the SDS slab gel thereby causing the proteins from the tube to further separate along the planar orientation of the slab gel. The glass plates are then removed from the medium and separated proteins and stained. The staining process makes the proteins visible to the naked eye revealing a two dimensional pattern of spots.

An automated apparatus and method for 2-D separations of proteins is described in greater detail in U.S. Pat. No. 5,993,627 to Anderson et al. and is incorporated by reference in its entirety. U.S. Pat. No. 5,993,627 includes a detailed description of sample preparation, electrophoresis procedures and staining of 2-D gels such that a plurality of separated proteins are visible after staining. Specifically, after staining, each separated protein produces a dark spot that is visible to the naked eye and can further be photographed by a camera or other video medium such as a computer imaging scanner. FIG. 1 is an electronically scanned image of one such 2-D gel showing a plurality of spots, each spot representing a protein or in some areas, a pair of proteins that migrated to the same isoelectric focusing point.

Serious study has been given to the relative locations of separated proteins on 2-D gels. Specifically, it is well known that from any give tissue sample, the proteins of that sample will migrate during the electrophoretic process to specific locations on the 2-D gel relative to other proteins thereby defining a recognizable pattern of spots. For instance, a sample taken from tissue of a rat's liver subjected to a reproducible 2-D electrophoretic process produces a recognizable pattern of spots, each spot formed by one or possibly two proteins. Repeated study of gel spot patterns for various tissues has subsequently led to the development of master patterns of spots, at least one master pattern for each tissue, where each master pattern visually represents the specific relative locations of the spots (relative to each other) within the recognizable pattern of spots. An example of a master pattern is shown in FIG. 2.

Although not shown in FIG. 2, information for each spots includes: a unique identifying number (also known as a master spot number or MSN), an (x,y) coordinate identifying the relative center of the identified spot on an (x,y) grid assigned to the gel image; a x-axis width, a y-axis width, and computer pixel intensity of the center of the spot. In addition to the recognizable pattern of spots, identification of many of the individual proteins at numerous spot locations has been added to each master pattern. Specifically, many of the spots in the gel pattern have been analyzed to determine the exact molecular composition of that protein.

A master pattern may be based upon the study of a healthy tissue, a treated tissue (treated with pharmaceuticals), diseased tissue and/or combinations thereof. In other words, the master pattern may include spot specific information obtained from the combined results of study of healthy tissue, treated tissue and diseased tissue or portions thereof.

The study of new pharmaceutical products often requires comparison of treated animal tissue with untreated animal tissue. Using the master pattern for guidance, a comparison can then be made of 2-D gels produced from treated tissues with other 2-D gels from a comparison set. The 2-D gels produced from treated tissues can yield important data concerning the effects of the new pharmaceutical on the tissues being studied. Specifically, some proteins in the treated tissues may not be present in the master pattern (untreated tissue) and conversely, some proteins in the master pattern (untreated tissue) may not be present in the treated tissue. Additionally, differences in the amount of protein between treated and control samples can yield important information about the effects of the pharmaceutical on the tissue.

Similarly, the study of diseased tissue also often requires comparison of the diseased tissue with healthy tissue. 2-D electrophoresis gels produced from healthy tissue are typically used to generate a master pattern for that tissue. A comparison can then be made between 2-D gels produced from diseased tissue and 2-D gels from healthy tissue. Some proteins in the healthy tissues may not be present in the diseased tissue and conversely, some proteins in the diseased tissue may not be present in the healthy tissue, and there may be quantitative differences in amount of certain proteins. Such information provides markers for detecting the corresponding disease.

One tool used for analyzing a 2-D gel involves image manipulation by a computer to warp two images into alignment with one another. Warping refers to a process of applying geometric corrections to modify the shape of features in an image and to change their spatial relationships. Another term used for a warping process is rubber-sheeting because the warping process can be likened to stretching a rubber sheet wherein portions of one or more images are stretched or shrunk in order to bring the spots on all the images into registration with one another and still maintain relative positional relationships between the spots.

Although images have been warped together to provide visual information about a 2-D gel, there is a need for technology wherein a master pattern is warped to an image in order to provide information about a 2-D gel based upon the information in the master pattern.

SUMMARY OF THE INVENTION

One object of the invention is to provide a reliable method and apparatus for providing spot specific data concerning the spots in a 2-D electrophoresis gel.

In accordance with one aspect of the present invention, a method for processing visual information from an image of a 2-D electrophoresis gel includes having a master pattern in digital form, scanning the image thereby converting the scanned image from visual information into digital form, comparing the scanned image with information from the master pattern, and outputting numeric data based upon the comparison.

Preferably, the visual information includes a plurality of spots defining a pattern of spots, each spot representing at least one protein.

Preferably, an object pattern is created from the scanned image and spot data in the master pattern is matched with spots represented in the object pattern. Using the matched spots, the master pattern is warped into alignment with the object pattern thereby creating a new object pattern from the master pattern. The new object pattern is augmented with spots in the object pattern not present in the master pattern. The parameters of the spots in the new object pattern are then modified by an optimization procedure to fit a processed image derived from the scanned image.

Preferably, the outputted information includes spot specific data such as:

an indication of presence of spots in the scanned image not found in the master pattern;

an indication of the absence of spots in the scanned image found in the master pattern;

an indication of the master spot number for spots in the new object pattern;

an indication of the location of spots in the new object pattern;

an indication of x and y dimensions of spots in the new object pattern;

an indication of the intensity of spots in new object pattern; and an indication of the integrated density of spots in the new object pattern.

In another aspect of the present invention, a computer is programmed to perform the steps of the method described above.

DETAILED DESCRIPTION OF THE PREFERRED EMBODIMENTS

Figure 3:
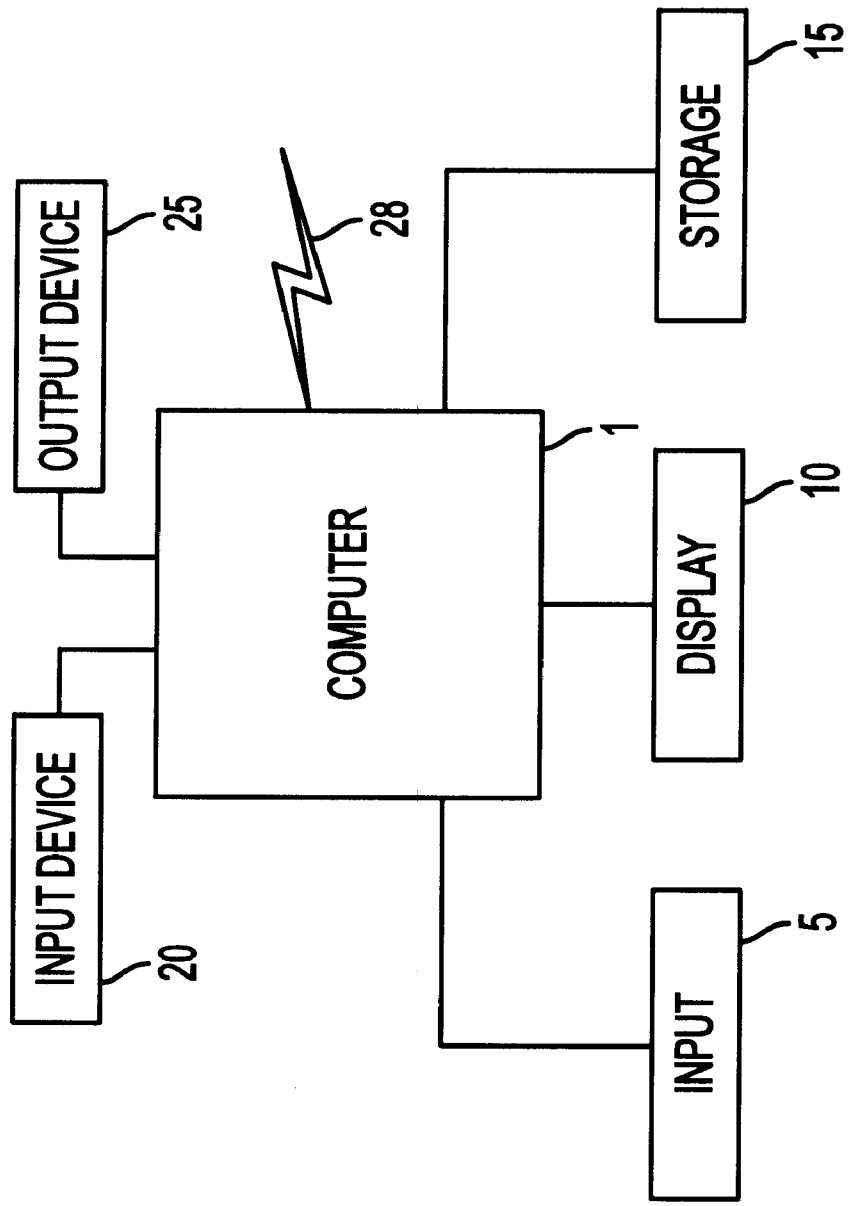
FIG. 3 shows a computer, various computer accessories and an input device for scanning or otherwise inputting an image into the computer for analysis in accordance with the present invention.

In accordance with one embodiment of the present invention, a computer 1 depicted in FIG. 3, is connected to an input 5, a display 10, a storage device 15, a digital input device 20, an output device 25 and a communications link 28. The computer 1 can be, for instance, a personal computer having RAM, ROM, a CPU, (not shown) and other standard internal personal computer hardware. The input 5 can be any of a variety of devices, such as a keyboard, mouse or similar data input and selecting device. The display 10 can be, for instance, a color monitor. The storage device 15 can be an internal storage device such as a hard disk drive able to store large amounts of digital data, or can alternatively be an external storage device such as an external hard drive, and/or a removable disk drive device such as a CDROM drive, MO drive or ZIP drive.

The input device 20 can be any of a variety of devices such as a digital camera, scanner or other image replicating device capable of providing an image in digitized form for input and manipulation by the computer 1. The output device 25 can be a printer, plotter or an external storage device that allows data to be outputted for entry into another computer or other data manipulation device. The communications link 28 can be any of a variety of communication configurations that allow communications between at least two computers, such as an Internet connection, modem, local area network (LAN) or the like.

Figure 1:
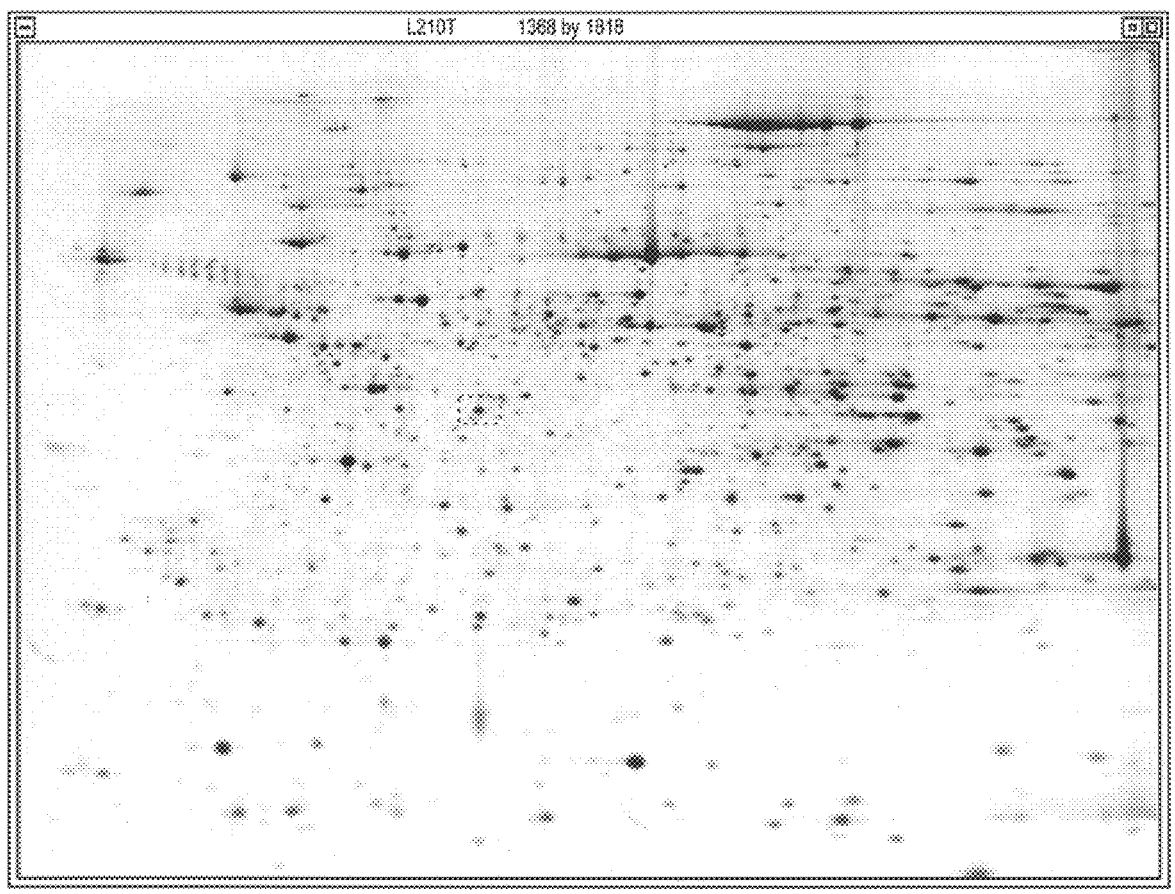
FIG. 1 is a scan of a 2-D gel having a plurality of stained spots that indicate the locations of various proteins separated during electrophoresis.

The image of the 2-D gel in FIG. 1 is generated using the input device 20 and thereafter inputted into the computer 1 as digital data. In accordance with the present invention, the digital information obtained from the gel image in FIG. 1 is processed and manipulated by the computer 1 in order to produce meaningful data based upon computer recognizable information such as the size, intensity, presence and/or absence of identified spots in the gel image, in a manner described in greater detail below.

Figure 4:
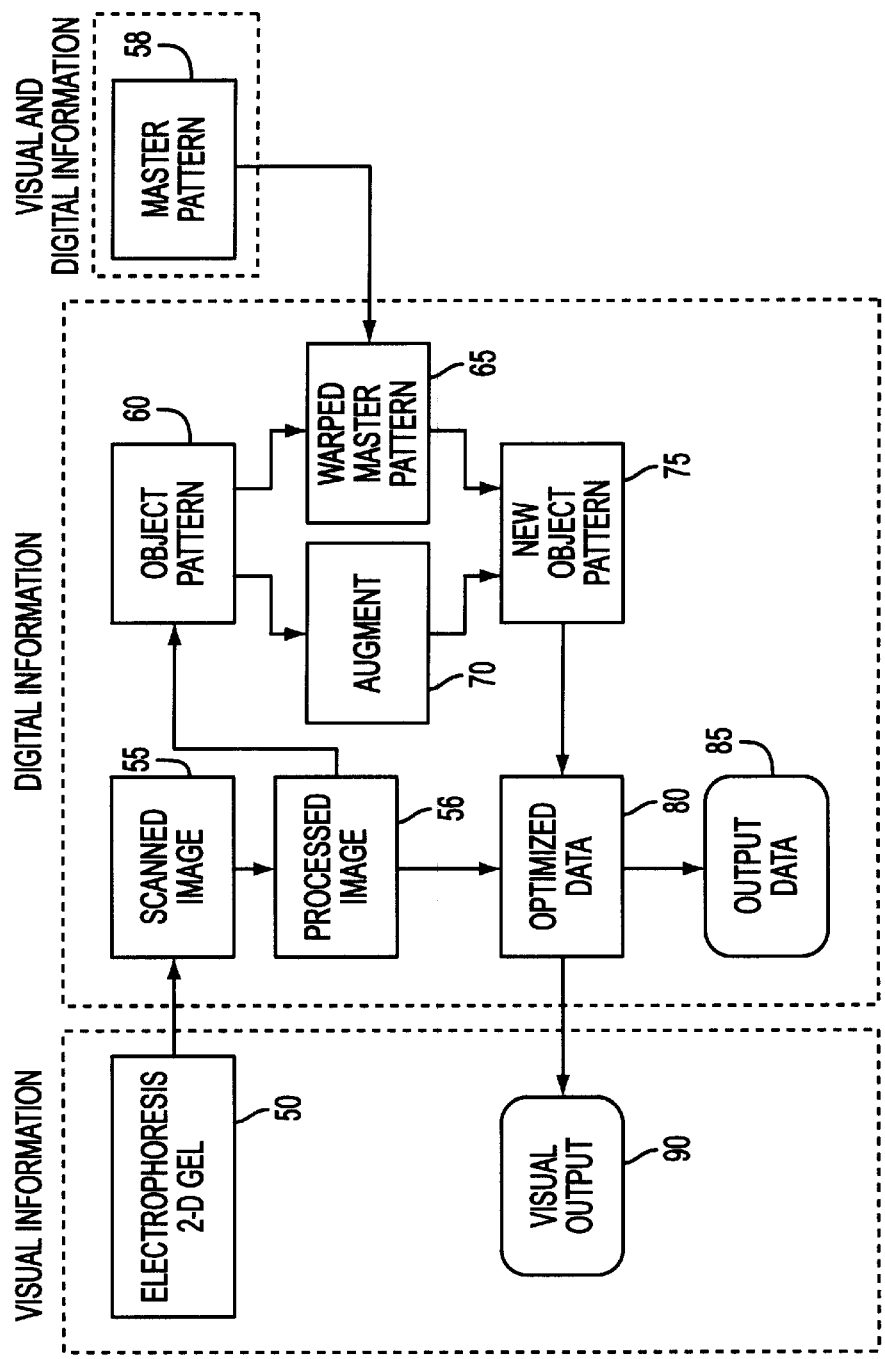
FIG. 4 is a schematic flowchart showing a representation of the flow of data manipulated by the computer shown in FIG. 3 for impressing information in the master pattern on to the scanned image in accordance with the present invention.
Figure 5:
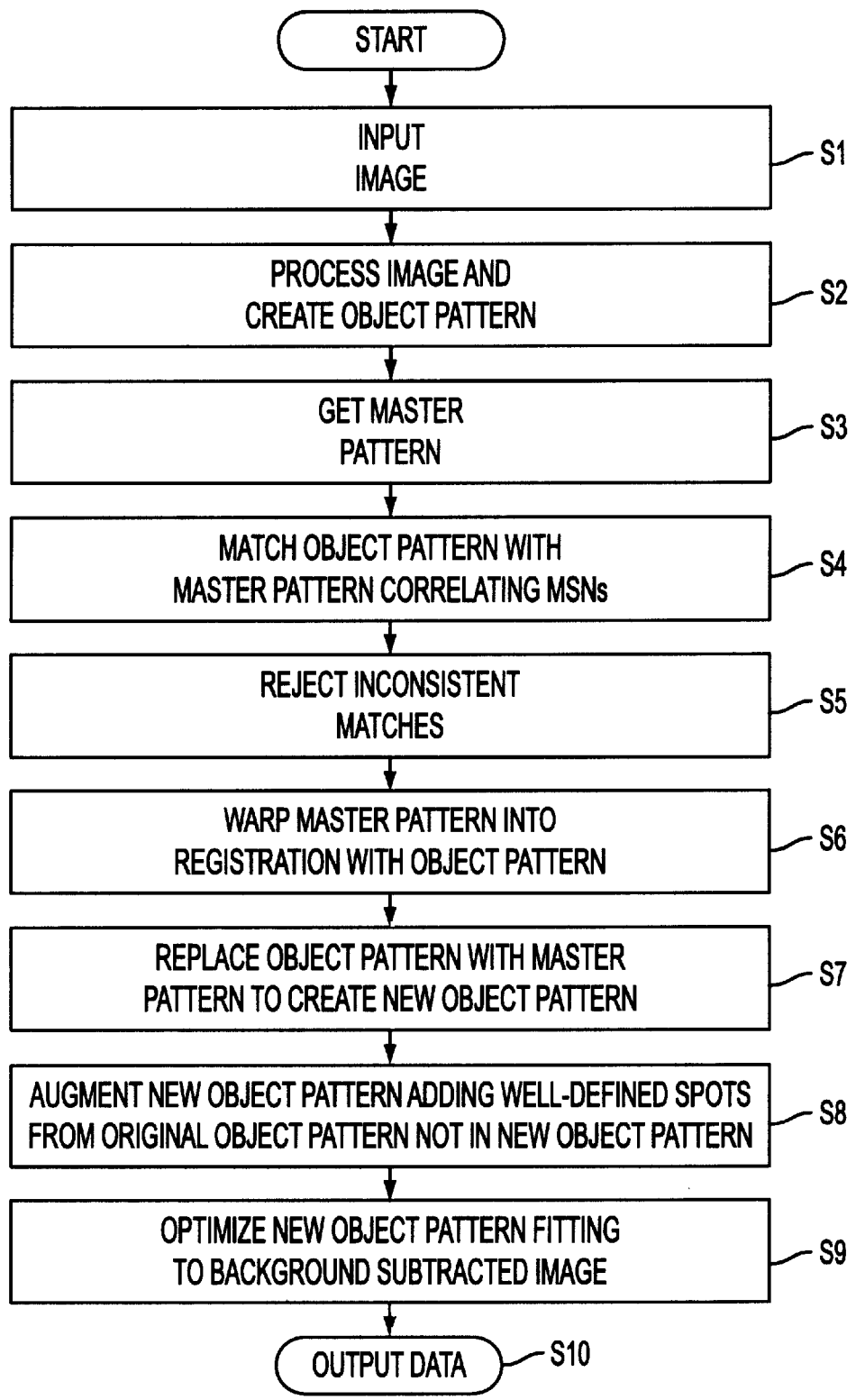
FIG. 5 is a flowchart showing various steps performed by the computer for impressing the master pattern on to the scanned image in accordance with the present invention.

FIG. 4 represents the general flow of data in and out of the computer 1. FIG. 5 depicts an operational flowchart that shows operations of the present invention within the computer 1. Both FIGS. 4 and 5 are explained in greater detail below. In order to provide a clearer explanation of the present invention, FIGS. 4 and 5 are explained together. FIG. 4 represents the flow of data as it is manipulated by the computer 1, and FIG. 5 represents the general operational steps performed by the computer 1. It should further be understood that the flowchart in FIG. 5 cannot adequately represent the operational steps performed by the computer because many of the steps are performed in a generally simultaneous manner, and therefore the actual order of the steps is not exact, as will be understood more clearly from the following description.

As mentioned above, the image in FIG. 1 is produced by scanning a 2-D gel 50 (shown schematically in FIG. 4). The 2-D gel 50 is produced by any of a variety of electrophoresis processes, such as, for instance, the process described in U.S. Pat. No. 5,993,627, to Anderson et al., which is incorporated herein by reference in its entirety. After electrophoresis, the 2-D gel 50 is scanned by the input device 20 of the computer 1 (FIG. 3). As mentioned above, the input device 20 can be a scanner digital camera, or other image replicating device capable of providing an image in digitized form for input and manipulation by the computer 1. However, the input device 20 may alternatively be connected to a separate computer (not shown) and the scanned image of the 2-D gel 50 can be inputted into the computer by, for instance, transmission over the communications link 28, or can be inputted via a computer diskette via the storage device 15.

Figure 6:
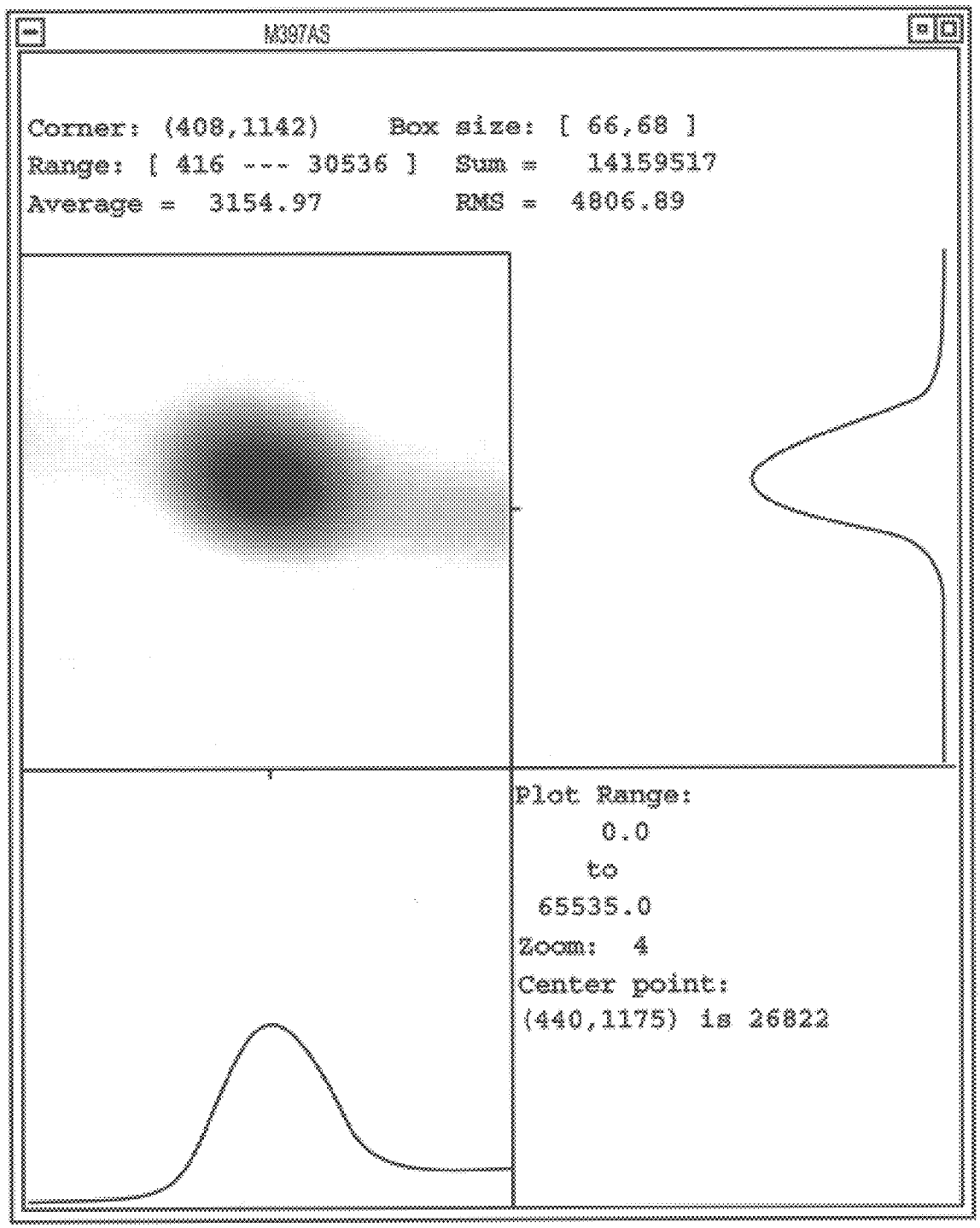
FIG. 6 is a portion of a scanned gel image processed by the computer shown with x and y-axis graphical gaussian representations that indicate x and y axis dimensions identified by the computer in accordance with the present invention.

Regardless of how the image of the 2-D gel 50 is generated, a scanned image 55 (FIG. 4) is inputted into the computer 1 based upon the 2-D gel 50. The 2-D gel depicted in FIG. 1 is visual information that is readily recognized by the human eye. However, the scanned image 55 is digital information held within memory and subsequently manipulated by the computer 1 in a manner described below. The computer 1 analyzes the scanned image 55 subtracting background and optionally filtering to reduce noise and artifacts thus generating a processed image 56. This processed image is further analyzed to detect and measure each recognizable spot. For instance, each spot in the processed image 56 is recognized to generate numeric data relating to size, location relative to other spots, and intensity or amplitude of the spot. FIG. 6 shows a single spot isolated from the spots in the gel depicted in FIG. 1. The size and intensity of the single spot have been analyzed pixel by pixel to produce two gaussian curves, as shown in FIG. 6, shown along the x-axis and the y-axis of the portion of the image shown. It should be understood that the computer apparatus and methods of the present invention do not necessarily produce the two gaussian curves shown in FIG. 6. The two gaussian curves shown in FIG. 6 are provided to assist in explaining the invention, but are not required to practice the invention because the information manipulated by the computer 1 is internal. The computer 1 only produces visual data as an option.

The computer 1 generates the following information relating to each spot in the scanned image 55 and processed image 56: x and y location; x-axis width; y-axis width; amplitude; and integrated density of the spot in processed image 56. These data are stored in the object pattern 60. It should be understood that the amplitude represents the intensity of the spot, for instance, as represented in the gaussian curves in FIG. 6. Integrated density of is the integral or area under the x-curve and the y-curve depicted in FIG. 6 for each spot. Alternatively, the integrated density is the sum of the individual pixel values in the processed image for each spot.

Inputting of the scanned image 55 is represented at step S1 in FIG. 5. At step S2, in FIG. 5, the scanned image is processed to produce the processed image 56 and an object pattern 60. It should be understood that a visual image of the object pattern can be produced, but is not necessary because there is further processing of the data.

Figure 2:
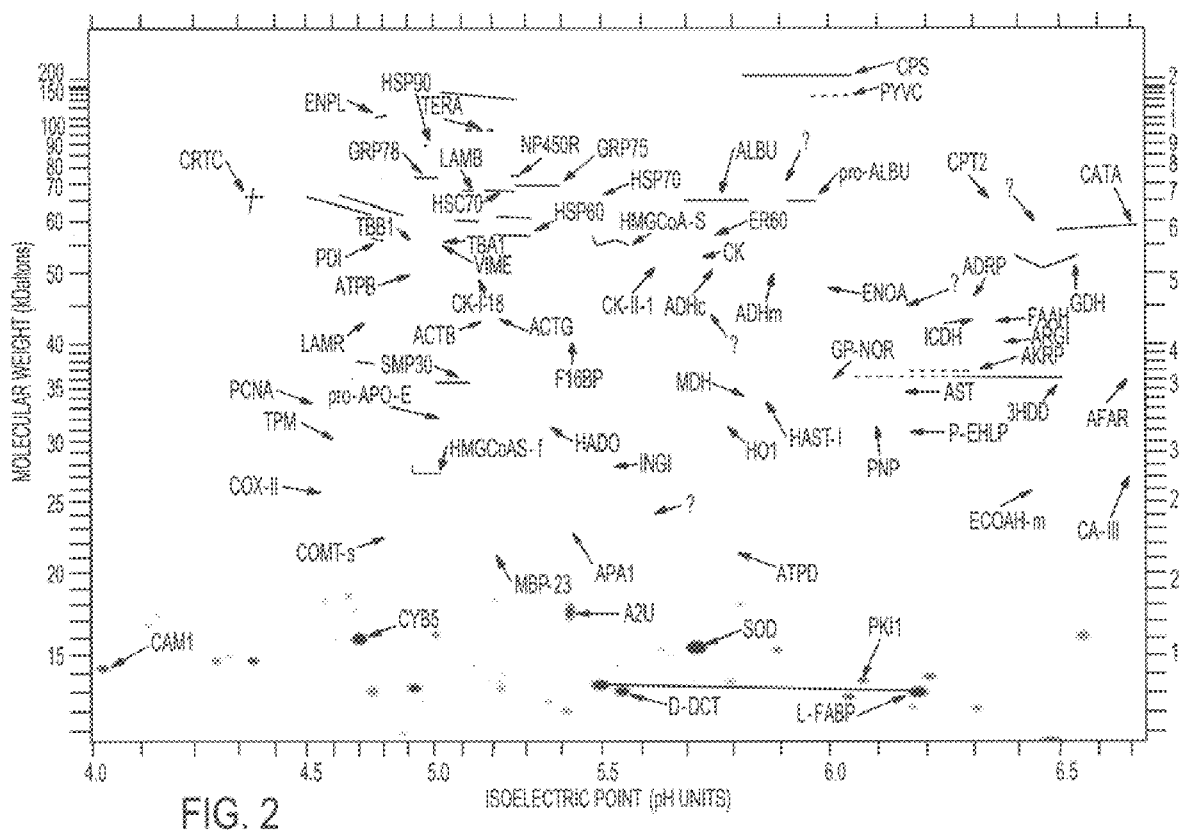
FIG. 2 is a master pattern of an untreated or healthy tissue corresponding to a like tissue sampled and subjected by electrophoresis to produce the 2-D electrophoresis gel depicted in FIG. 1, the master pattern showing relative locations of protein spots, relative sizes, intensities, and master spot numbers for many of the protein spots of the untreated or healthy tissue.

The computer 1 also obtains a master pattern 58 from memory or from the storage device 15, as indicated at step S3 in FIG. 5. The master pattern 58 is typically maintained as both visual and digital information. For instance, the master pattern depicted in FIG. 2 is visual information but is also maintained as digital information including x and y relative locations of each spot in the master pattern, x widths, y widths and amplitudes for each of the spots in the master pattern. Further, the master pattern 58 also includes master spot numbers MSNs for each spot in the pattern. It should be understood that steps S1, S2 and S3 may occur in any order and in practice generally occur simultaneously.

As indicated at step S4, the spots in the object pattern 60 are further analyzed in order to match up the spots in the object pattern 60 with the corresponding spots in the master pattern 58. The master pattern 58 includes spot specific information accumulated from the study of healthy, treated tissue, and/or diseased tissue that was sampled and studied in order to generate 2-D gels, as was mentioned above. The gel 50, scanned image 55 and object pattern 60 are produced from a sample of, for instance, pharmaceutically treated tissue or diseased that corresponds to the tissue studied for creation of the master pattern 58. Therefore the computer 1 easily recognizes many of the spots that are common to both the master pattern 58 and the object pattern 60 because both were generated from the same type of tissue (for example, rat liver).

The computer 1 matches the spots in the master pattern 58 and the object pattern 60 by considering the relative locations of the various spots, the amplitude and widths of the spots. The matching process at step S4 is imperfect but does provide a fairly close matching of spots. However, since the master pattern 58 and the object pattern 60 both represent a like tissue, the spots between the two patterns are located at proximate relative positions.

After the computer 1 has made matches between spots in the object pattern 60 and the master pattern 58, some of the inconsistent matches of spots are rejected, as indicated at step S5. The rejection of inconsistent matches includes rejection of matched spots that are not in close x and y alignment to each other by a predetermined distance. The rejection may be a result of background noise in the original gel 50. For instance, the gel 50 has streaks that may prevent precise localization of spots. Matches with such streaks and spots on the master pattern 58 are rejected so that they do not damage the warping process, described below.

Matching of spot locations between the object pattern 60 and the master pattern 58 provides location links between the master pattern 58 and the object pattern 60. Consequently, spot locations in the master pattern 58 are warped into alignment with the spot locations in the object pattern 60, as is indicated at step S6 in FIG. 5. The warping process involves applying geometric corrections to modify the positions (the (x,y) coordinates) of each of the spots in the master pattern to bring the locations of the spots into alignment with the matching spots in the object pattern 60. The warping process can be likened to stretching a rubber sheet wherein portions of the master pattern 58 are stretched or shrunk in order to bring the spots in the master pattern 58 into alignment with the matched spots in the object image 60. Many applicable procedures for warping may be found in DIGITAL IMAGE WARPING by George Wolberg, IEEE Computer Society Press, Los Alamitos Calif., 1990, which is also incorporated herein by reference. The warped master pattern 65 is indicated in FIG. 4 as being digital data since at this point no visual data is outputted. However, it should be understood that the warped master pattern 65 can be outputted if desired.

A new object image 75 is now created, as indicated at step S7 in FIG. 5. The new object image 75 includes each of the spots in the warped master pattern 65 and is augmented by the addition of spots from the object pattern 60 not found in the warped master pattern 65. Specifically, in step S7, the warped master pattern 65 replaces the object pattern 60 to become a new object image 75. The new object image 75 includes all of the (x,y) locations of the spots in the warped master pattern 65 and further includes the x widths, y widths, amplitudes and MSNs from the warped master pattern 65. Further, as indicated at step S8 in FIG. 5, the new object pattern 75 is augmented by the addition of well-defined spots in the object image 60 that are not present in the warped master pattern 65.

At steps S7 and S8, the computer 1 compares the warped master pattern 65 and the object pattern 60 and identifies all well-defined spots in the object pattern 60 that are not present in the warped master pattern 65. Since the warped master pattern 65 includes many spots that have been matched and warped to spots in the object pattern 60, identification of well-defined spots not present in the warped master pattern 65 is generally straight forward. The computer 1 compares the spot specific information for those portions of the warped master pattern 65 and the object pattern 60 not matched in step S4. Unmatched spots in the object pattern 60 that are clearly well defined are added to the new object pattern 75 at step S8.

The new object pattern 75 therefore includes all of the spot information from the warped master pattern 65, including master spot numbers (MSNs) and also include unidentified spots from the object pattern 60. It should be understood that steps S7 and S8 are generally performed simultaneously and are therefore not necessarily performed in the order shown in FIG. 5.

At step S2, as described above, the scanned image 55 is processed. However, the processing at step S2 is not limited to the operations described above. Specifically, the scanned image 55 is also processed to subtract background and any artifacts to generate the processed image 56. The new object pattern 75 is optimized or fitted to the processed image 56 to more reliably bring the spots in the new object pattern 75 into alignment or registration with the scanned image 55, as is indicated at step S9 in FIG. 5. As mention above, the matching at step S4 is imperfect and imprecise. Therefore, the warping process in step S6 is equally imprecise. Therefore, the optimizing step S9 is desirable in order to provide a more reliable fit of the spot data in the new object pattern 75 to the processed image 56. The fitting process produces the optimized data 80 shown in FIG. 4.

At step S9 in FIG. 5, the optimization process also includes adding spot specific information from the processed image 56 to the new object pattern 75 in order to provide data for outputting. Specifically, each spot identified in the processed image is measured to provide an x-width, a y-width and an amplitude representing the intensity of the spot image. The x-width, y-width and amplitude are added to the new object pattern 75 replacing the data originally retained from the master pattern 58. The outputted data 85 therefore includes: spot locations (x,y) for each spot based upon the locations in the processed image 56; the x-width from the processed image 56; the y-width from the processed image 56; the amplitude from the processed image 56; the integrated density of the spot from the processed image 56; the MSN for those spots matched with spots from the master pattern 58.

At step S10 in FIG. 5 data is generated and output as either visual data 90 or digital data 85, as indicated in FIG. 4. The visual data 90 is not a scanned image, but rather a rendering of the spot specific data into a visual format. Specifically, the computer 1 uses the (x,y) coordinates to locate the spots on the monitor of the computer 1, then uses the x and y-width and amplitude data to reproduce the spots on the monitor. Further, those spots that were matched to the data in the master pattern 58 are shown with the master spot number (MSN). In this manner a visual representation of the processed information is possible.

The data outputted at box 85 in FIG. 4 is alpha-numeric data that includes a list of the spots in the optimized data 80. Specifically, the outputted data 85 includes: spot locations (x,y) for each spot based upon the locations in the processed image 56; the x-width from the processed image 56; the y-width from the processed image 56; the amplitude from the processed image 56; the integrated density of the spot from the processed image 56; and the MSN for those spots derived from the master pattern 58.

The outputted data 85 is now ready for comparison to the master pattern 58 or data from other separations. Since the data is processed in a systematic manner, outputs from a plurality of experiments can be compiled for comparison and analysis. The outputted data 85 may also be used as a basis for comparison to the original scanned image 55. The outputted data 85 includes an alpha-numeric output for each spot present in the optimized data 80. This data is spot specific data (SSD).

One of the many advantages of the present invention is the identification of new spots in a gel not in a master pattern and also the identification of spots not present in a gel that are present in the master pattern. For instance, the spot identified as D-DCT is present at the bottom of the master pattern in FIG. 2 and is also present in the scanned image in FIG. 1. However, the spot to the immediate left of spot D-DCT does not appear in the gel in FIG. 1 indicating some difference in the activity of the tissue sample from the samples that were used to generate the master pattern. For the scanned gel in FIG. 1, the output 85 would indicate the absence of the spot next to spot D-DCT.

The spot specific data of the output 85 also includes the x width, y width, amplitude and integrated density for each spot in the scanned image 55 (derived from the processed image 56) but also includes the MSN identifying various spots. Using the spot specific data in the output 85 it is possible to detect and measure difference in the size and intensity of the spots from two samples of a tissue, for instance a sample from a healthy tissue and a sample from a treated or diseased tissue.

The output 85 therefore provides a variety of data that is used to make further determinations about protein production in a tissue. Using the computer and methods of the present invention it is possible to receive data that indicates the presence or absence of a protein and/or the change in concentration of a protein in a 2-D gel as compared with the information from other 2-D gels.

The methods of the present invention can be summarized as follows.

The present invention relates generally to a method for processing visual information from an image of a 2-D electrophoresis gel and includes several basic steps. Specifically, a master pattern in provided in digital form to the computer 1. An image of a 2-D gel is scanned and inputted into the computer 1 thereby converting the scanned image from visual information into digital form. The scanned image is then processed and combined with information from the master pattern in order to provide an output that includes numeric data.

In the method of the present invention, the visual information includes a plurality of spots defining a pattern of spots, each spot representing at least a portion of one protein. The method further includes creation of an object pattern from the processed imaged derived from the scanned image. Spot data in the master pattern is then matched with spots in the object pattern. The matched spots between the master pattern and the object pattern provide location links making it possible to warp the master pattern into alignment with the object pattern. The warped master pattern is then used to create a new object pattern. The new object pattern is then augmented with the addition of spots in the object pattern not present in the master pattern and then optimized to fit the processed image data.

The content of the new object pattern includes spot specific data. The spot specific data includes for every spot: an (x,y) coordinate; an x-width; a y-width; an amplitude; an integrated density; a MSN if the spot is found in the master pattern. An indication of presence of spots in the scanned image not found in the master pattern and an indication of the absence of spots in the scanned image found in the master pattern can be inferred by a quick examination of the pattern.

The information outputted can be used for a variety of purposes. For example, some of the analyzed spot information can be used to identify spots that are to be cut from the gel used to make the scanned image. The cut spots can then be subjected to mass spectrometry or other analysis.

The present invention provides a means for rapidly identifying spots in a 2-D electrophoresis gel that warrant further study. The present invention further provides a means for determining the overall concentration of certain spots in a 2-D electrophoresis gel that are markers for disease or indicate drug interaction.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A method for processing visual information from an image of a 2-D electrophoresis gel, further comprising the steps of:

having a master pattern in digital form;

scanning the image thereby converting the image from visual information into digital form, said visual information comprising a plurality of spots defining a pattern of spots, each spot representing at least a portion of one protein;

creating an object pattern from the scanned image or an image derived from the scanned image;

matching spot data in the master pattern with spots represented in the object pattern;

warping the master pattern into alignment with the object pattern thereby creating a new object pattern from the master pattern;

augmenting the new object pattern with spots in the object pattern not present in the master pattern;

comparing the scanned image with information from the augmented object pattern; and outputting numeric data based upon the comparison in said comparing step.

2. A method for processing visual information as set forth in claim 1, wherein in said comparing step, the scanned image is compared to the new object pattern.

3. A method for processing visual information as set forth in claim 1, wherein in said comparing step, the new object pattern is fitted to a processed image based upon the scanned image bringing each spot in the new object pattern into more precise alignment with the spots in the scanned image.

4. A method for processing visual information as set forth in claim 3, wherein in said comparing step, the size and width of each spot in the new object pattern present in the processed image is replaced with the size and width of each corresponding spot in the processed image.

5. A method for processing visual information as set forth in claim 1, wherein said outputting step comprises outputting spot specific data.

6. A method for processing visual information as set forth in claim 5, wherein the spot specific data comprises:

an indication of presence of spots in the scanned image not found in the master pattern;

an indication of the absence of spots in the scanned image found in the master pattern; x-widths and y-widths of spots in the scanned image; master spot numbers for at least a portion of the spots in the scanned image; amplitude of spots in the processed image; and integrated density of spots in the processed image.

7. A method for processing image data. from a 2-D gel, comprising the steps of:

providing an appropriate tissue specific master pattern;

creating an object pattern representing spots in an image of a 2-D gel protein separation from the appropriate tissue;

matching spots in the object pattern with corresponding spots in the master pattern;

rejecting matches or identification inconsistent with other matches;

warping the master pattern to the object pattern to align matched spots;

replacing the object pattern with warped master pattern to create a new object pattern;

augmenting the new object pattern by adding well-defined spots in original object pattern not accountable in new object pattern;

optimizing the new object pattern fitting to a processed image based on the scanned image; and outputting information based upon said optimizing step.

8. A method for processing image data as set forth in claim 7, wherein the spots in the scanned image define a recognizable pattern of spots, each spot representing at least a portion of one protein.

9. A method for processing image data as set forth in claim 8, wherein said outputting step comprises outputting spot specific data.

10. A method for processing image data as set forth in claim 9, wherein the spot specific data comprises:

an indication of presence of spots in the scanned image not found in the master pattern;

an indication of the absence of spots in the scanned image found in the master pattern;

x-widths and y-widths of spots in the processed image;

master spot numbers for at least a portion of the spots in the scanned image;

amplitude of spots in the processed image; and integrated density of spots in the processed image.

11. An apparatus for processing data comprising a computer having means for inputting data and scanning images, said apparatus being configured to perform the following steps:

processing a master pattern in digital form;

scanning an image thereby converting the scanned image from visual information into digital form, wherein said visual information comprises a plurality of spots defining a pattern of spots, each spot representing at least a portion of one protein;

fitting information from the master pattern to information in the scanned image;

creating an object pattern from the scanned image;

matching spot data in the master pattern with spots represented in the object pattern;

warping the master pattern into alignment with the object pattern thereby creating a new object pattern from the master pattern;

augmenting the new object pattern with spots in the object pattern not present in the master pattern;

comparing the scanned image with the augmented object pattern; and outputting numeric data based upon the comparison in said comparing step.

12. An apparatus as set forth 11, wherein said outputting step comprises outputting spot specific data.

13. An apparatus as set forth 12, wherein the spot specific data comprises:

an indication of presence of spots in the scanned image not found in the master pattern;

an indication of the absence of spots in the scanned image found in the master pattern;

x-widths and y-widths of spots in the scanned image;

master spot numbers for at least a portion of the spots in the scanned image;

amplitude of spots in the processed image; and integrated density of spots in the processed image.

14. A method for processing visual information from an image of a 2-D electrophoresis gel, comprising the steps of:

having a master pattern in digital form;

scanning the image thereby converting the image from visual information into digital form, wherein said visual information comprises a plurality of spots defining a pattern of spots, each spot representing at least a portion of one protein;

creating an object pattern from the scanned image or an image derived from the scanned image;

matching spot data in the master pattern with spots represented in the object pattern;

warping the master pattern into alignment with the object pattern thereby creating a new object pattern from the master pattern;

augmenting the new object pattern with spots in the object pattern not present in the master pattern;

comparing the scanned image with information from the master pattern; and outputting numeric data based upon the comparison in said comparing step.

* * * * *